(12) United States Patent
Hayashi

(10) Patent No.: US 8,333,114 B2
(45) Date of Patent: Dec. 18, 2012

(54) MICROSTRUCTURE INSPECTING DEVICE, AND MICROSTRUCTURE INSPECTING METHOD

(75) Inventor: Masato Hayashi, Amagasaki (JP)

(73) Assignee: Tokyo Electron Limited (JP)

( * ) Notice: Subject to any disclaimer, the term of this patent is extended or adjusted under 35 U.S.C. 154(b) by 254 days.

(21) Appl. No.: 12/744,873

(22) PCT Filed: Nov. 26, 2008

(86) PCT No.: PCT/JP2008/071471
§ 371 (c)(1),
(2), (4) Date: Jun. 3, 2010

(87) PCT Pub. No.: WO2009/069670
PCT Pub. Date: Jun. 4, 2009

(65) Prior Publication Data
US 2010/0307248 A1 Dec. 9, 2010

(30) Foreign Application Priority Data
Nov. 26, 2007 (JP) ................. 2007-304597

(51) Int. Cl.
*G01N 29/12* (2006.01)
(52) U.S. Cl. .......................... 73/597; 73/579
(58) Field of Classification Search ........... 73/597, 73/579, 584, 649–651, 655, 658, 663; 367/140, 367/142; 310/334, 336, 338
See application file for complete search history.

(56) References Cited

U.S. PATENT DOCUMENTS

| | | | |
|---|---|---|---|
| 5,520,052 A * | 5/1996 | Pechersky | 73/579 |
| 6,595,058 B2 | 7/2003 | Lai et al. | |
| 6,907,787 B2 * | 6/2005 | Cook et al. | 73/700 |
| 7,383,732 B2 * | 6/2008 | Okumura et al. | 73/602 |

(Continued)

FOREIGN PATENT DOCUMENTS

JP 04-178538 6/1992

(Continued)

OTHER PUBLICATIONS

International Search Report—PCT/JP2008/071471 dated Feb. 24, 2009.

(Continued)

*Primary Examiner* — J M Saint Surin
(74) *Attorney, Agent, or Firm* — Cantor Colburn LLP

(57) ABSTRACT

A microstructure inspecting device 10 which measures a damping characteristic value of a moving portion of a microstructure includes a pressure wave generating device 1 and a pulse generating device 2 which apply an impact to the moving portion without directly contacting the microstructure, and a vibrometer 4 which measures a displacement of the moving portion for a predetermined period of time after the start of free vibration of the moving portion without contacting the moving portion. The pressure wave generating device 1 is a sound wave generating element of thermal excitation type, a piezoelectric sound wave generating element, or an electromagnetic vibration element, and is driven by a pulse signal of the pulse generating device 2. The pressure wave generating device 1 using the sound wave generating element of thermal excitation type may include a thermally conductive substrate, a heat-insulating layer formed of nano-crystal silicon in one principal surface of the substrate, an insulating layer formed on the heat-insulating layer, and a conductive layer formed on the insulating layer and emitting heat when being supplied with current containing alternating current components.

8 Claims, 12 Drawing Sheets

U.S. PATENT DOCUMENTS

| | | | |
|---|---|---|---|
| 7,726,190 B2 * | 6/2010 | Matsumoto et al. | 73/602 |
| 7,872,394 B1 * | 1/2011 | Gritters et al. | 310/309 |
| 8,103,593 B2 * | 1/2012 | Kim | 705/59 |
| 2007/0151341 A1 * | 7/2007 | Mazza et al. | 73/579 |
| 2008/0190206 A1 | 8/2008 | Matsumoto et al. | |

FOREIGN PATENT DOCUMENTS

| | | |
|---|---|---|
| JP | 05-034371 | 2/1993 |
| JP | 06-118070 | 4/1994 |
| JP | 2004-523768 | 8/2004 |
| JP | 2005-114376 | 4/2005 |
| JP | 2006-220637 | 8/2006 |
| JP | 2007-108157 | 4/2007 |
| JP | 2007-144406 | 6/2007 |
| JP | 2007-285904 | 11/2007 |
| WO | 2006-093232 | 9/2006 |
| WO | 2007/003952 | 1/2007 |

OTHER PUBLICATIONS

Chinese Office Action—Chinese Application No. 200880117854.0 issued on Oct. 24, 2011, citing WO 2006/93232, WO 2007/003952, and JP 2007-144406.

* cited by examiner

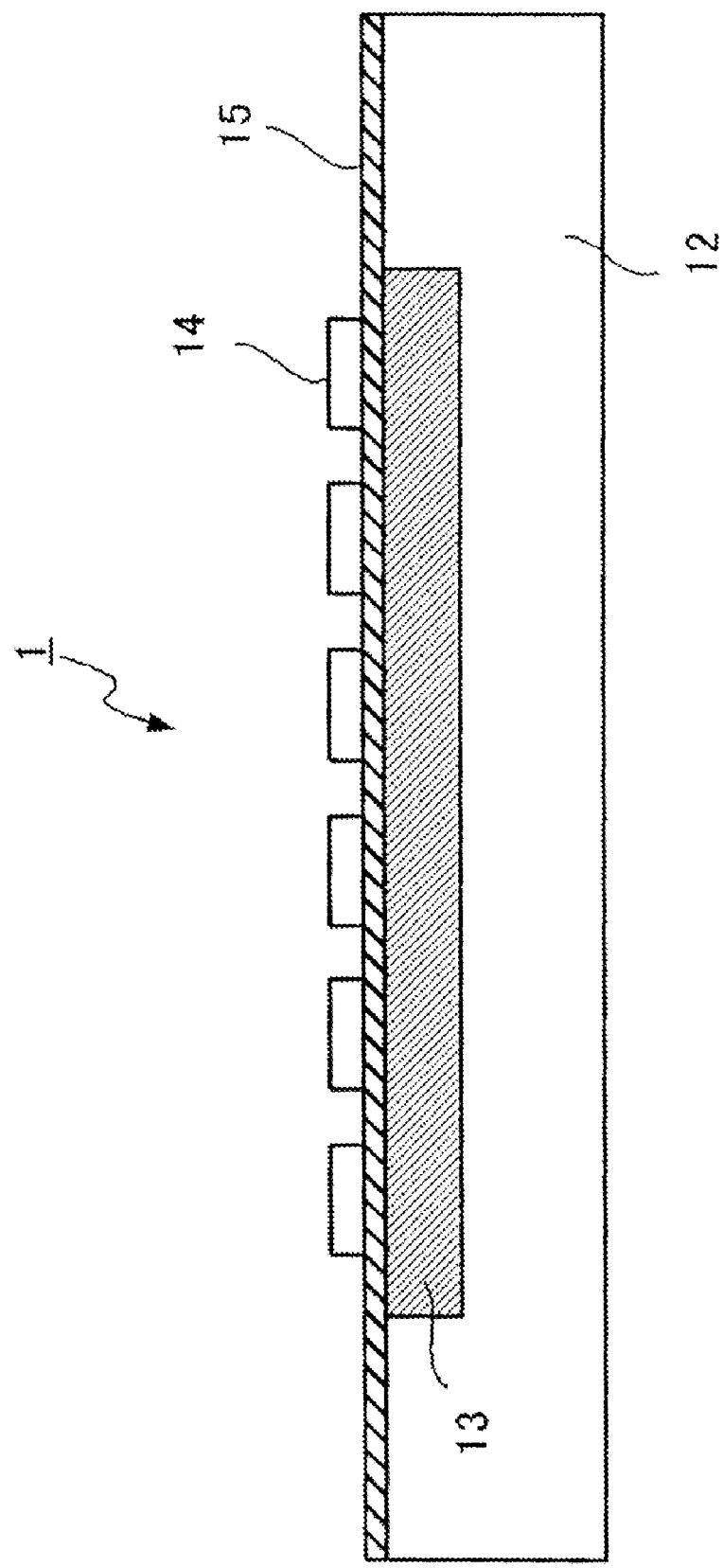

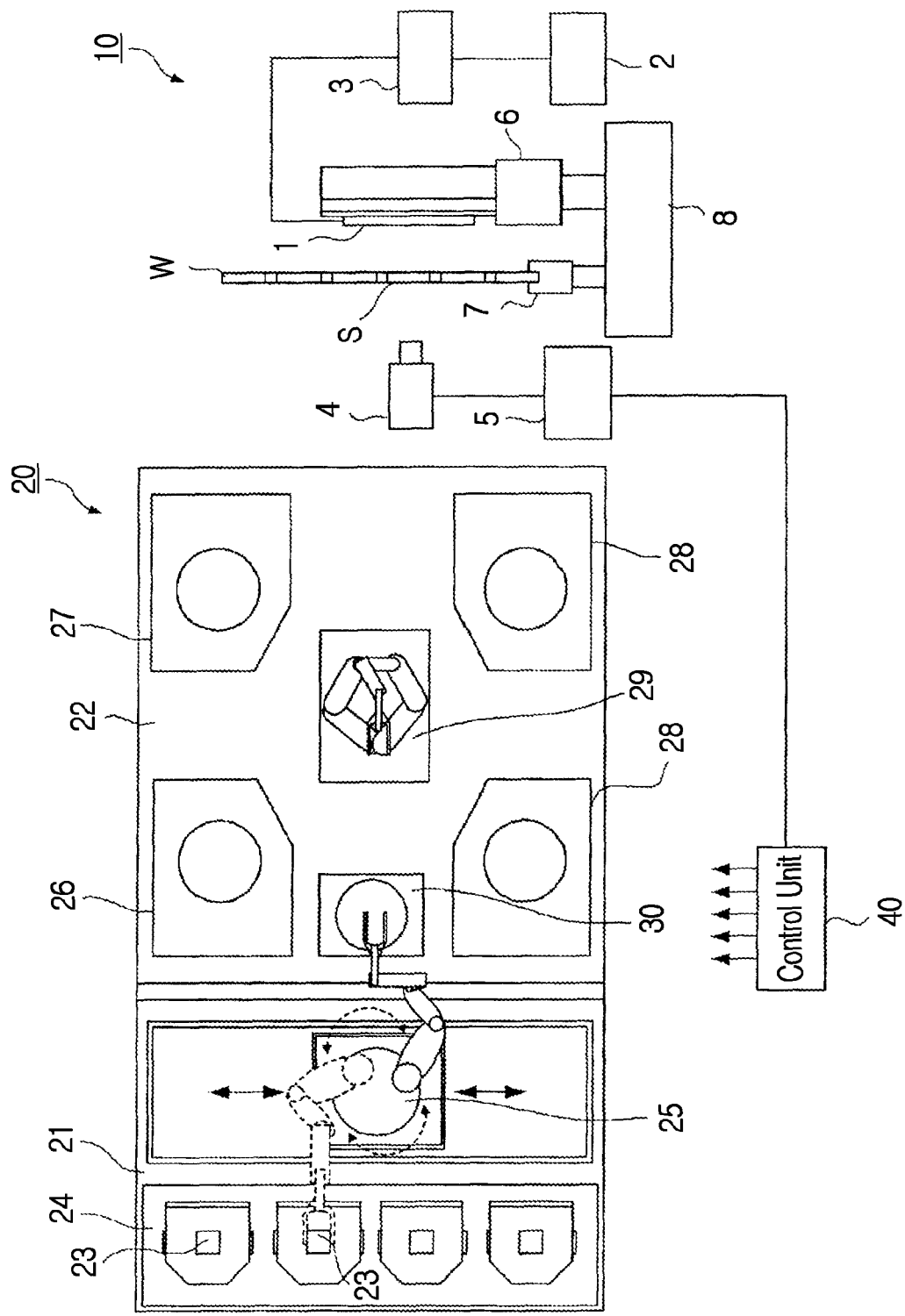

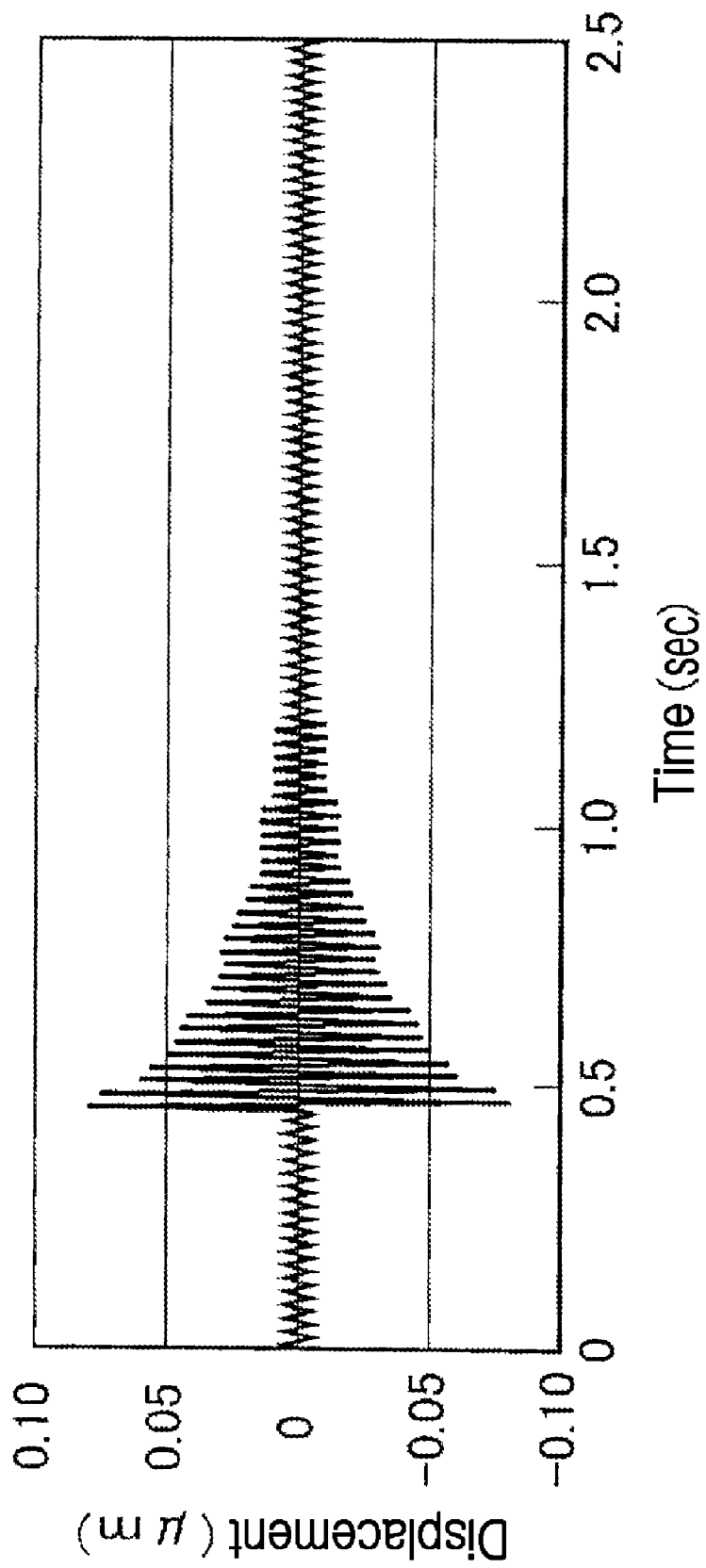

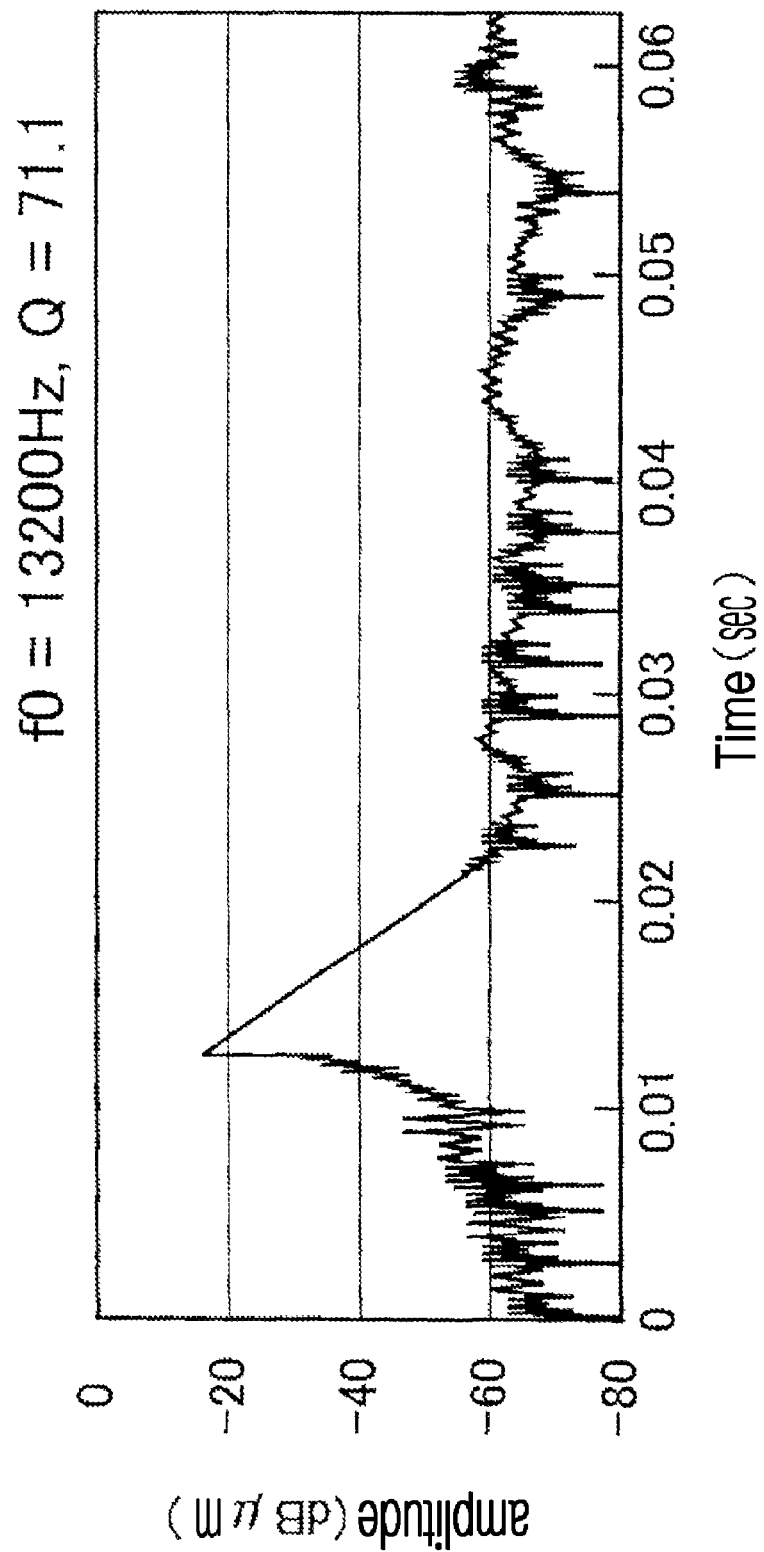

MICROSTRUCTURE INSPECTING DEVICE, AND MICROSTRUCTURE INSPECTING METHOD

TECHNICAL FIELD

The present invention relates to a device and method for inspecting a microstructure including a moving portion.

BACKGROUND ART

Recently, microstructure devices, for example, various sensors using MEMS (Micro Electro Mechanical Systems), have been used in various fields including automobile and medical technology. As electronic devices have been made small and light and have high-level functions, the development of MEMS has also been promoted. Since MEMS are micro-fabricated systems, there is a demand for an appropriate method of inspecting the MEMS.

Examples of a method of measuring mechanical characteristics, such as an attenuation factor ($\zeta$), a Q value, a natural frequency (f0), and a loss factor ($\tau$), of a microstructure include a method of obtaining a decay curve by using an impulse hammer, and a method of obtaining a resonance frequency by intentionally scanning an excitation frequency of a structure and thus obtaining an attenuation factor from a FWHM (Full Width at Half Maximum) of a resonance curve.

Patent Document 1 or Patent Document 2 discloses a method of causing a test sound wave to be output from a speaker to a moving portion of a sensor to move the moving portion, and thus inspecting electrical characteristics of a microstructure by using a probe. Patent Document 3 discloses a method of detecting a change in the resistance value of an acceleration sensor formed on a wafer by blowing air and thus determining the property of the acceleration sensor.

Also, Patent Document 4 discloses a method of outputting an ultrasonic wave to a moving portion to induce slow dynamics on an object, and measuring a physical change. Also, Patent Document 5 discloses a method of intermittently generating a longitudinal wave by using a sound wave generating element of thermal excitation type, and thus detecting a distance to an object and an orientation where the object is located. Also, Patent Document 6 discloses a method of causing a PZT (lead zirconate titanate) ultrasonic wave transforming device to directly contact a microstructure, and thus measuring a dynamic response.

(Patent Document 1) Japanese Laid-Open Patent Publication No. 2007-108157
(Patent Document 2) International Publication No. 2006/093232 Pamphlet
(Patent Document 3) Japanese Laid-Open Patent Publication No. Hei 5-34371
(Patent Document 4) Japanese Laid-Open Patent Publication No. 2004-523768
(Patent Document 5) Japanese Laid-Open Patent Publication No. 2006-220637
(Patent Document 6) Specification of U.S. Pat. No. 6,595,058

DISCLOSURE OF THE INVENTION

Technical Problem

The method using the impulse hammer indirectly moves the moving portion by passing through a support member of the microstructure and a support unit of the moving portion of the microstructure, and the like. Accordingly, since the impact time or intensity of impact to be applied to the moving portion cannot be precisely controlled, the degree of measurement precision of the decay curve is not high. Also, with respect to a DUT (die under tester: chip-state sample) having a low Q value, since an impact time and a decay time are almost the same, damping characteristics or the Q value cannot be measured. Also, the method disclosed in the Patent Document 6 cannot directly excite the moving portion of the microstructure. Accordingly, vibration of a package (PKG) or a support case body overlaps with a signal line or reverberation of an impact source overlaps, thereby resulting in a decrease in the degree of measurement precision.

With respect to a DUT having a low Q value, although the method of applying a pressure to the moving portion of the sensor with a sound wave without using the impulse hammer can directly excite the moving portion of the microstructure to enable measurement, there exists the influence of reverberation of a speaker of a sound source. With respect to a DUT having a high Q value, the method of scanning the frequency is difficult to have a sufficient number of measurement points for FWHM.

Since electrical characteristics of the microstructure are inspected by using the impulse hammer, the microstructure cannot be directly excited, and thus the microstructure has been excited in the form of a package (PKG). Accordingly, since defective products can be detected only in a final step of a manufacturing process, even though defects occur in the middle of the manufacturing process, the manufacturing process proceeds to the final step, thereby leading waste of time and money. Also, defect analysis and solution on defects is delayed, thereby reducing efficiency.

The present invention is proposed considering the aforementioned state of art. According to the present invention a microstructure inspecting device and method capable of precisely and reproducibly controlling impact time and intensity and performing measurement with a high degree of precision may be provided.

Technical Solution

To solve the problems, according to an embodiment of the present invention, there is provided a microstructure inspecting device which measures a damping characteristic value of a moving portion of a microstructure, the microstructure inspecting device including an impact applying unit which applies an impact to the moving portion by using a pressure wave generation device that does not directly contact the microstructure; and a measuring unit which measures a displacement of the moving portion for a predetermined period of time after the start of free vibration of the moving portion, without contacting the moving portion.

Preferably, the impact applying unit may include a sound wave generating element of thermal excitation type, and a driving unit which inputs a pulse signal to the sound wave generating element.

Preferably, the sound wave generating element of thermal excitation type may include a thermally conductive substrate; a heat-insulating layer formed of nano-crystal silicon in one principal surface of the substrate; an insulating layer formed on the heat-insulating layer; and a conductive layer formed on the insulating layer and emitting heat when being supplied with current containing alternating current components.

To solve the problems, according to another embodiment of the present invention, there is provided a microstructure inspecting method including: applying an impact to a moving portion of a microstructure by using a pressure wave generating device that does not directly contact the microstructure; causing the moving portion to freely vibrate; and measuring a displacement of the moving portion during a predetermined period of time after the start of the free vibration of the moving portion, without contacting the moving portion.

Preferably, the pressure wave generating device may be a sound wave generating element of thermal excitation type.

Preferably, the sound wave generating element of thermal excitation type may include a thermally conductive substrate; a heat-insulating layer formed of nano-crystal silicon in one principal surface of the substrate; an insulating layer formed on the heat-insulating layer; and a conductive layer formed on the insulating layer and emitting heat when being supplied with current containing alternating current components.

Preferably, the microstructure inspecting method may further include calculating a Q value of the microstructure from the displacement of the moving portion measured in the measuring step; and determining that the microstructure is normal when the Q value is within a predetermined range, and determining that the microstructure is defective when the Q value is not within the predetermined range.

Preferably, the microstructure inspecting method may further include feeding back the Q value calculated in the calculating step, and a determined result in the determining step to a control device that sets a manufacturing condition of a manufacturing device for manufacturing the microstructure.

Advantageous Effects

According to the microstructure inspecting device of the present invention, since impact time or intensity can be precisely and reproducibly controlled, the degree of measurement precision of vibration damping characteristics of a microstructure is improved.

BRIEF DESCRIPTION OF THE DRAWINGS

FIG. 2B is a cross-sectional view of the pressure wave generating device according to the embodiment of the present invention.

FIG. 3 is a block diagram showing an example of a configuration of the manufacturing system including a microstructure inspecting device according to the embodiment of the present invention and a semiconductor manufacturing device.

FIG. 4 is a graph showing an damped vibration pattern of a first embodiment.

FIG. 9B is a second graph showing a spectrum obtained by Hilbert transform in the second embodiment.

BEST MODE FOR CARRYING OUT THE INVENTION

Figure 1:
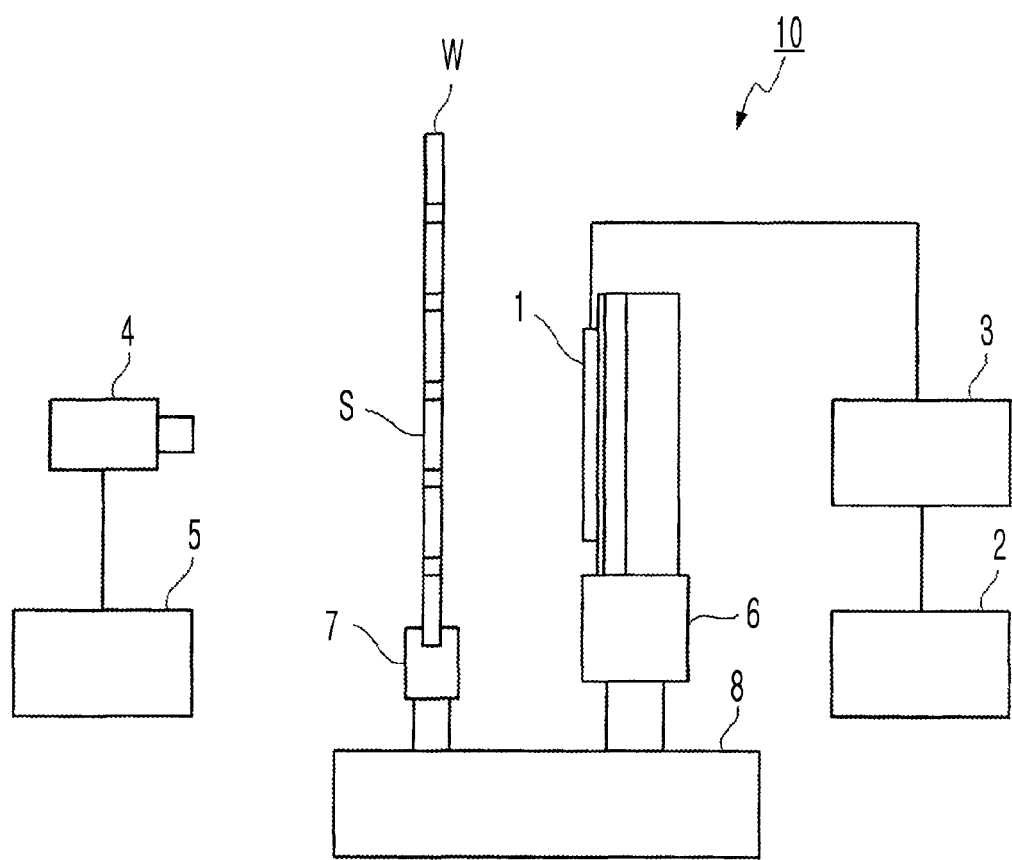
FIG. 1 is a block diagram showing an example of a configuration of a microstructure inspecting device according to an embodiment of the present invention.
Figure 2A:
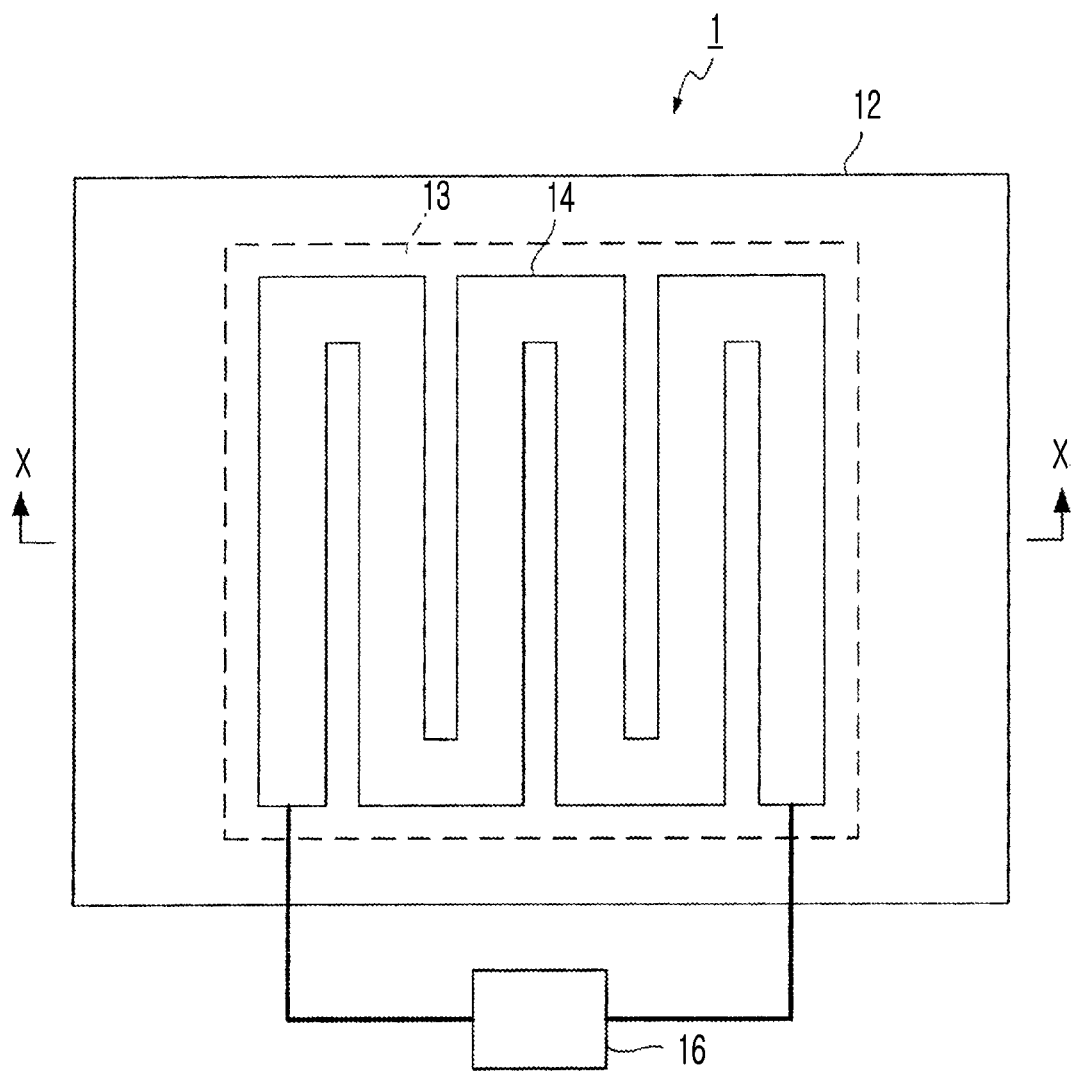
FIG. 2A is a plan view of a pressure wave generating device according to the embodiment of the present invention.

Herein below, embodiments of the present invention will be explained in detail with reference to the drawings. Also, the same or corresponding elements in the drawings are denoted by the same reference numerals, and a repeated explanation thereof will not be given. FIG. 1 is a block diagram showing an example of a configuration of a microstructure inspecting device according to an embodiment of the present invention. FIG. 2A is a plan view showing connection of a driving circuit of a pressure wave generating device 1 shown in FIG. 1. FIG. 2B is a cross-sectional view taken along line X-X of FIG. 2A.

As shown in FIG. 1, a microstructure inspecting device 10 includes the pressure wave generating device 1, a pulse generating device 2, an amplifying unit 3, a vibrometer 4, a calculating unit 5, a support unit 6, a chuck 7, and an inspecting stage 8. The pressure wave generating device 1 is supported by the support unit 6 and is installed on the inspecting stage 8. A sample S is placed to face a surface of the pressure wave generating device 1 on which a pressure wave is generated, and a wafer W having the sample S is supported by the chuck 7.

The microstructure inspecting device 10 according to the present embodiment used the pressure wave generating device 1 in order to excite the sample S. A sound wave generating element of thermal excitation type is used in order to generate a pressure wave, and uses a longitudinal wave, which is generated by heating and cooling air by using a heater, as a sound wave. Accordingly, impact time or intensity can be precisely and reproducibly controlled by using the heater. Since a speaker including a vibration plate having elasticity and mass is not used, there is no risk of reverberation. Also, if the mass of the vibration plate is negligible and a moving portion can vibrate without contacting the sample S, a piezoelectric sound wave generating element may be used in order to generate a pressure wave. Also, by forming a coil around a microstructure, an impact may be directly applied to the sample S by exciting the coil through electromagnetic induction.

As shown in FIGS. 2A and 2B, the pressure wave generating device 1 includes a substrate 12, a heat-insulating layer 13, a heating element 14, and an insulating layer 15. A driving circuit 16 is electrically connected to both ends of the heating element 14. The substrate 12 is formed of bulk silicon or the like. The heat-insulating layer 13 formed of porous nano-crystal silicon (hereinafter, referred to as nc-Si) is formed in one principal surface of the substrate 12. The insulating layer 15 is formed in the surface of the substrate 12, in which the heat-insulating layer 13 is formed, to contact the heat-insulating layer 13. The insulating layer 15 is formed of a thin film of an insulating material such as silicon nitride ($Si_3N_4$), silicon dioxide ($SiO_2$), aluminum oxide ($Al_2O_3$), or the like. The heating element 14 having a heater pattern is formed of a thin film of a electrically conductive metal, for example, tungsten (W), platinum (Pt), or gold (Au), to contact a top of the insulating layer 15.

The driving circuit 16 applies an intermittent pulse voltage, or an alternating current voltage, at a predetermined frequency w to both ends of the heating element 14. The thickness of the heat-insulating layer 13, with respect to alternating current components of the voltage applied to the heating element 14, is about the same as a thermal diffusion length determined by the thermal conductivity and heat capacity per unit volume of the heat-insulating layer 13. Accordingly, alternating current components of emitted heat to the substrate 12 side are insulated and direct current components of the emitted heat generated due to the heat capacity of the heating element 14 may efficiently diffuse to the substrate 12 having high thermal conductivity. If the heat-insulating layer 13 is formed of nc-Si, although the thickness of the heat-insulating layer 13 may vary according to a frequency of a sound wave generated, the thickness of the heat-insulating layer 13 may range, for example, from about 5 µm to about 200 µm.

The thickness of the insulating layer 15 is sufficiently less than the thermal diffusion length, and thus the alternating current components of the emitted heat of the heating element 14 are insulated in a thickness direction of the heat-insulating layer 13. The insulating layer 15 conducts heat in a surface direction. Since the heating element 14 is closely attached to the insulating layer 15, the insulating layer 15 operates to make the temperature of the heating element 14 uniform. Since the insulating layer 15 does not allow electricity to pass therethrough, the insulating layer 15 does not emit heat, and reduces local thermal stress of the heating element 14 by making the temperature of the heating element 14 uniform. Accordingly, even with a voltage leading to breaking of wire which a conventional pressure wave generating device may encounter, the heating element 14 rarely undergoes deformation or breaking of wire. As a result, it is possible to increase the sound pressure of a sound wave generated by the pressure wave generating device 1.

It is preferable that the insulating layer 15 has high thermal conductivity in an in-plane direction, and does not absorb heat in a thickness direction. Accordingly, the insulating layer 15 may be thinly formed of a material having high thermal conductivity and low specific heat. The insulating layer 15 may be formed of a material, for example, magnesium oxide (MgO), diamond crystalline carbon (C), aluminum nitride (AlN), or silicon carbide SiC as well as the aforesaid silicon nitride ($Si_3N_4$), silicon dioxide ($SiO_2$), or aluminum oxide ($Al_2O_3$). The thickness of the insulating layer 15 ranges, for example, about 50 nm to about 200 nm.

The heating element 14 is not limited to a specific material if the heating element 14 is formed of a metal film. For example, the heating element 14 may be formed of a metal simple substance such as tungsten (W), molybdenum (Mo), iridium (Ir), gold (Au), aluminum (Al), nickel (Ni), titanium (Ti), and platinum (Pt), or a stacked structure thereof. The heating element 14 may be formed by vacuum deposition, sputtering, or the like. Also, although it is preferable that the thickness of the metal film is as small as possible in order to reduce heat capacity, the thickness of the film may be selected from a range of 10 nm to 300 nm in order to have appropriate resistance.

Now, a process of forming the pressure wave generating device 1 will be explained with reference to FIG. 2B. First, the substrate 12 of a silicon wafer is prepared, and an electrode layer formed of a thin film of, for example, aluminum, is formed on an inner surface by vacuum deposition or the like. Next, anodizing is performed by using a mixture solution of hydrofluoric acid (HF) and ethanol on a portion where the heat-insulating layer 13 is to be formed by using platinum (Pt) as a counter electrode. The heat-insulating layer 13 having a desired thickness and grain size and formed of porous nc-Si is formed by controlling a component ratio of the solution, current density, and a processing time to have predetermined values. The insulating layer 15 is formed on the surface of the substrate 12 in which the heat-insulating layer 13 is formed. Non-doped silicate glass (NSG) or the like is deposited on the substrate 12 by using, for example, plasma CVD, to form the insulating layer 15.

For example, a stencil mask S patterned to have the shape of the heating element 14 is held on the insulating layer 15, and the heating element 14 is formed to have a predetermined pattern on the insulating layer 15 by gold (Au) sputtering. Next, an electrode or the like for connecting the driving circuit 16 to the heating element 14 is formed, and the electrode layer formed on the inner surface undergoes removal, polishing, or the like if necessary.

Referring to FIGS. 1, 2A, and 2B again, a microstructure inspecting order in the present embodiment of the present invention will be explained. A voltage transmitted from the pulse generating device 2 is amplified to become a plurality of pulse voltages or a pulse voltage having a desired time width by the amplifying unit 3, and is applied in burst shape to the heating element 14 of the pressure wave generating device 1. The heating element 14 generates a pressure wave of an impulse by heating and cooling an ambient air layer, and radiates the pressure wave to the sample S to excite the sample S. Due to the excitation, a moving portion of the sample S starts damped vibration. The vibration of the moving portion is measured by using the vibrometer 4, for example, a non-contact type laser vibrometer.

Since the pressure wave generating device 1 can precisely and reproducibly control impact time or intensity, a sound pressure enough to measure can be obtained, thereby increasing the degree of measurement precision. Also, the pressure wave generating device 1 does not have the influence of reverberation of an impulse source when the pressure is applied, thereby not having the influence of noise. Also, since the pressure wave generating device 1 can directly excite the microstructure so that the microstructure does not have to contact the sample S to measure the amount of displacement, the pressure wave generating device 1 doesn't affect the damped vibration of the moving portion.

The amount of displacement measured by the vibrometer 4 may be calculated as an damped vibration pattern by the calculating unit 5 to obtain a resonance frequency or a Q value. If the obtained value is not within a predetermined numerical range, it is determined that there is abnormality and thus good products and defective products can be distinguished.

A Q value, which is a dimensionless number primarily indicating the state of vibration, is related to loss of energy due to absorption by a medium, in the propagation of elastic waves. In vibration, the Q value is energy obtained by dividing energy stored in a system during one period by energy dissipated in the system, where a larger Q value indicates greater vibration stability. If the Q value is high, it means that the state of vibration is stable, and a startup time is long and the distribution of vibration energy is high. A resonance frequency is obtained from a value obtained by converting a vibration pattern into a frequency spectrum by using Fourier transform. Also, a Q value is obtained from a gradient of a spectrum graph that is obtained by converting the vibration pattern by using Hilbert transform. For example, if an object to be inspected is a MEMS, it can be determined whether a spring constant of a moving portion of the MEMS is normal or not by using a resonance frequency. Also, structural defects in a pressure sensor, a gyro sensor, or the like can be detected by using a Q value.

FIG. 3 is a block diagram showing a configuration of a manufacturing system including a semiconductor manufacturing device and the microstructure inspecting device 10 according to the embodiment of the present invention. A representative semiconductor manufacturing process includes a pre-process and a post-process, wherein the pre-process includes a circuit design, a patterns design, a photomask making, a wafer manufacturing, and elements formation, and the post-process includes assembly, final inspection and marking. The semiconductor manufacturing device shown in FIG. 3 is a photolithography/etching processing device 20 of a microstructure (MEMS) (hereinafter, referred to as a processing device 20) and is used in the wafer manufacturing process.

The microstructure inspecting device 10 is the same as that shown in FIG. 1 and an explanation thereof will be omitted. The calculating unit 5 of the microstructure inspecting device 10 is connected to a control unit 40 of the processing device 20. The control unit 40 includes a calculation processing device and a ROM that stores a processing program and the like, and controls the whole processing device 20 and individual systems constituting the processing device 20.

The processing device 20 includes a cassette station 21 and a processing station 22. The cassette station 21 transfers wafers W, which are supplied from the outside in the unit of a wafer cassette, from cassettes 23 to the processing device 20, or transfers the wafers W having been processed from the processing device 20 to the cassettes 23. The processing station 22 includes a plurality of processing units, and performs photolithography/etching while sequentially moving the wafers W to each of the processing units.

A cassette holding stage 24 is formed in the cassette station 21, and one of the cassettes 23 in which a wafer W to be processed is stored is supplied from the outside. Also, in the cassette holding stage 24, a wafer W having been processed is stored in a cassette 23 to be transferred out. Transfer of a wafer W on the cassette holding stage 24 is performed by a station transfer mechanism 25. The station transfer mechanism 25 can move horizontally (in a direction marked by a solid arrow) and vertically (in a direction perpendicular to the ground) so as to access the plurality of cassettes 23 placed on the cassette holding stage 24. Also, the station transfer mechanism 25 can rotate (in a direction marked by a dotted arrow) so as to transfer the wafer W from the processing station 22 to the cassette holding stage 24.

A plurality of photolithography/etching processing units (processing units 26 through 28), a unit transfer mechanism 29, and a temporarily-holding stage 30 are formed in the processing station 22. A resist pattern is formed in the processing unit 26. Etching is performed in the processing unit 27. A film is formed and the resist is removed in the processing unit 28.

A wafer W transferred to the processing station 22 is placed on the temporarily-holding stage 30, and the unit transfer mechanism 29 starts to act as a transfer mechanism instead of the station transfer mechanism 25. Due to the unit transfer mechanism 29, the wafer W is sequentially transferred in the order of the processing unit 26, the processing unit 27, and the processing unit 28 so that photolithography/etching is performed on the wafer W. The wafer W on which the processing has been completed is placed on the temporarily-holding stage 30 again, and is transferred from the processing station 22 by the station transfer mechanism 25. The unit transfer mechanism 29 can move horizontally and vertically, and rotate, like the station transfer mechanism 25.

A resist pattern is formed in the processing unit 26. The wafer W transferred to the processing unit 26 is covered with a photomask due to a resist spread. The wafer W covered with the photomask is exposed and developed, to form a resist having a desired shape (pattern) on the wafer W. The resist is cured by heating to be adhered to the wafer W. If exposure or development is insufficient, the resist may be deformed to have a pattern other than the desired pattern.

Etching is performed in the processing unit 27. Although there are wet etching and dry etching, wet etching will be explained herein. The wafer W is immersed in an etching solution such as hydrogen fluoride or the like, and a portion of the wafer W not covered with the resist is etched. A portion of the wafer W protected by the resist is not etched and thus the same shape as the shape of the resist is bulgingly formed on the wafer W. An etching state varies according to the temperature or time of the etching solution, and also, as an etching depth increases, etching may occur even in a portion directly under the resist.

A film is formed and the resist is removed in the processing unit 28. In the formation of the film, a layer formed of a metal or an oxide film is formed on the wafer W by using vacuum deposition, sputtering, or the like. Next, the resist is completely removed by using a resist solvent or the like. Since a film formed on the resist is also removed during the removal of the resist, a desired pattern can be added to the upper surface of the wafer W.

In a microstructure having a complex structure, after processing in the processing unit 28, photolithography/etching is repeatedly performed in processing units (not shown) 26a, 27a, 28a through 26n, 27n, and 28n. Also, the microstructure is manufactured by machanoelectric conversion device formation, wire formation, and the like as well as performing photolithography/etching.

The wafer W in which the microstructure is formed is engaged on the microstructure inspecting device 10. The microstructure, which is a sample S, is located facing an output portion of the pressure wave generating device 1, and the wafer W is supported by the chuck 7. A voltage transmitted from the pulse generating device 2 is amplified to a plurality of pulse voltages or a pulse voltage having a desired time width by the amplifying unit 3, and is applied in a burst shape to the heating element 14 of the pressure wave generating device 1. The heating element 14 generates a pressure wave of an impulse by heating and cooling an ambient air layer, and radiates the pressure wave to the sample S to excite the sample S. Since the sample S is directly excited, there is no influence of reverberation or noise. Also, since the impact time or intensity of the pressure wave is precisely controlled, reproducibility is high. A moving portion of the sample S starts damped vibration due to the excitation. The vibration of the moving portion is measured by using the vibrometer 4, for example, a laser Doppler vibrometer.

Also, measuring of displacement of the sample S by the vibrometer 4 is performed for a predetermined period of time after the start of free vibration of the sample S. That is, the pressure wave generating device 1 (speaker) radiates the pressure wave to the sample S (the moving portion) to enable the sample S to vibrate. Next, the pressure wave generating device 1 stops the radiation of the pressure wave to the sample S to enable the sample S to freely vibrate. And, the vibrometer 4 measures the displacement of the sample S while the sample S is freely vibrating. Here, free vibration refers to vibration of the moving portion in a state where reverberation of the speaker or other peripheral equipment is zero or negligible. While the sample S is freely vibrating, external influence is zero. Accordingly, while the sample S is freely vibrating, only damping characteristics of the sample S can be purely measured. In particular, since a nano-crystal silicon speaker can reduce reverberation, the nano-crystal silicon speaker is suitable for such a measurement system.

A measured damped vibration pattern is numerically processed by the calculating unit 5 to calculate a resonance frequency and a Q value, and thus it is determined whether the microstructure is good or bad. If the resonance frequency exceeds a designated numerical range, it may be found that a spring constant of the moving portion of the microstructure is abnormal. If the Q value exceeds a preset range, it is found that the structure of a sensor is abnormal. For example, damage to the microstructure may be occurred or film thickness may be abnormal.

Analysis of causes of defects is performed based on abnormality in the resonance frequency or the Q value. If the resonance frequency is low, it is possible that the moving portion is small or the support unit is thin due to, for example, over-etching. Also, if the Q value is low, that is, if vibration is immediately reduced, it is possible that the microstructure is damaged. It is possible that the resist formation is not performed well, the wafer W is not sufficiently protected, the wafer W is excessively etched, and thus the resist fails to have a desired shape. Alternatively, since a film is not formed well, thick or thin film formation or the like may occur.

Information about the measured resonance frequency and the Q value of the microstructure is fed back from the calculating unit 5 to the control unit 40. If there is a feedback of information indicating that the value is out of a preset desired numerical range that means the microstructure is in a good state, conditions for predicted questions and corresponding solutions are set according to a state of abnormal value, so that a control instruction may be output to a corresponding system from the control unit 40. Also, a program of the control unit 40 may be previously set so that a buzzer sound or flash light is occurred from an external device connected to the control unit 40 to indicate abnormality. If both the resonance frequency and the Q value are abnormal, it is possible to set the processing station 22 to temporarily stops.

For example, if the resonance frequency is abnormal, it is possible that etching results are not in accordance with design. Accordingly, a control instruction is output from the control unit 40 to the processing unit 27 to suitably change etching conditions or the like. If the Q value is much different from a desired value, it is possible that damage to the microstructure is occurred. It is possible that the resist is not formed to have a desired shape and thus the resist fails to protect the wafer W during etching. A control instruction is transmitted from the control unit 40 to the processing unit 26 where the resist is formed, to suitably change conditions for photolithography, etc. In case that abnormality in the Q value of the microstructure manufactured after conditions in the processing unit 26 are changed occurs, it is highly possible that not in the formation of the resist but the formation of the film is abnormal. A control instruction is transmitted from the control unit 40 to the processing unit 28, to suitably change conditions for film formation.

Also, even when measurement results indicate good products, the trend of the manufacturing state may be kept track of by accumulating fed-back measurement data and repeatedly reflecting the measurement data. Also, when the measurement results indicate good products, adjusting various conditions by automatic control is helpful in performing the manufacturing process while maintaining product quality constant.

The wafer W of which measurement has been completed is transferred to a next process at the same time as the control unit 40 feeds back the measurement results. Accordingly, since processing conditions of the wafer W on which the microstructure is formed can be adjusted by automatic control from now on, generation of defective products can be prevented. Also, since the microstructure of which the resonance frequency and the Q value was abnormal is checked, the microstructure can be discarded after cutting off of a chip. Accordingly, defective products can be removed without bringing the manufacturing process to a final step.

As described above, since the microstructure inspecting method according to the present invention can precisely and reproducibly control impact time or intensity, the degree of measurement precision of vibration damping characteristics of a microstructure is improved. Also, it is helpful in performing the manufacturing process while maintaining product quality constant that measurement results are fed back to the control device. Also, since an inspection is not limited to a final step of the manufacturing process, defective products are reduced and efficient manufacturing can be achieved.

The microstructure inspecting device 10 according to the present embodiment used the pressure wave generating device 1 in order to excite the sample S. Although the sound wave generating element of thermal excitation type was used in order to generate the pressure wave, a coil may be formed on the microstructure and an impact may be directly applied to the sample S by exciting the coil due to electron induction.

Also, there may be changes or modifications in the configurations of the pressure wave generating device 1, or the microstructure inspecting device 10 using the pressure wave generating device 1 without being limited to the aforesaid embodiments, or there may be combinations of the devices. For example, selections or combinations of devices are not limited to those shown in FIG. 3, and in terms of hardware, any of various shapes, patterns, sizes, etc. may be arbitrarily selected, and in terms of software, any of program setting, particularly, setting of desired numerical ranges for good products, may be arbitrarily selected, according to objects to be measured. A process in which the inspection is to be performed in a manufacturing step is not limited to the embodiments and may be arbitrarily selected.

Next, as an example of an embodiment of the present invention, a measurement was performed in case that the sample S, which was an object to be inspected, was a pendulum of an acceleration sensor or a fishbone acoustic sensor. Embodiment 1 shows a case using the pendulum of the acceleration sensor, and Embodiment 2 shows a case using the fishbone acoustic sensor.

Embodiment 1

Figure 5:
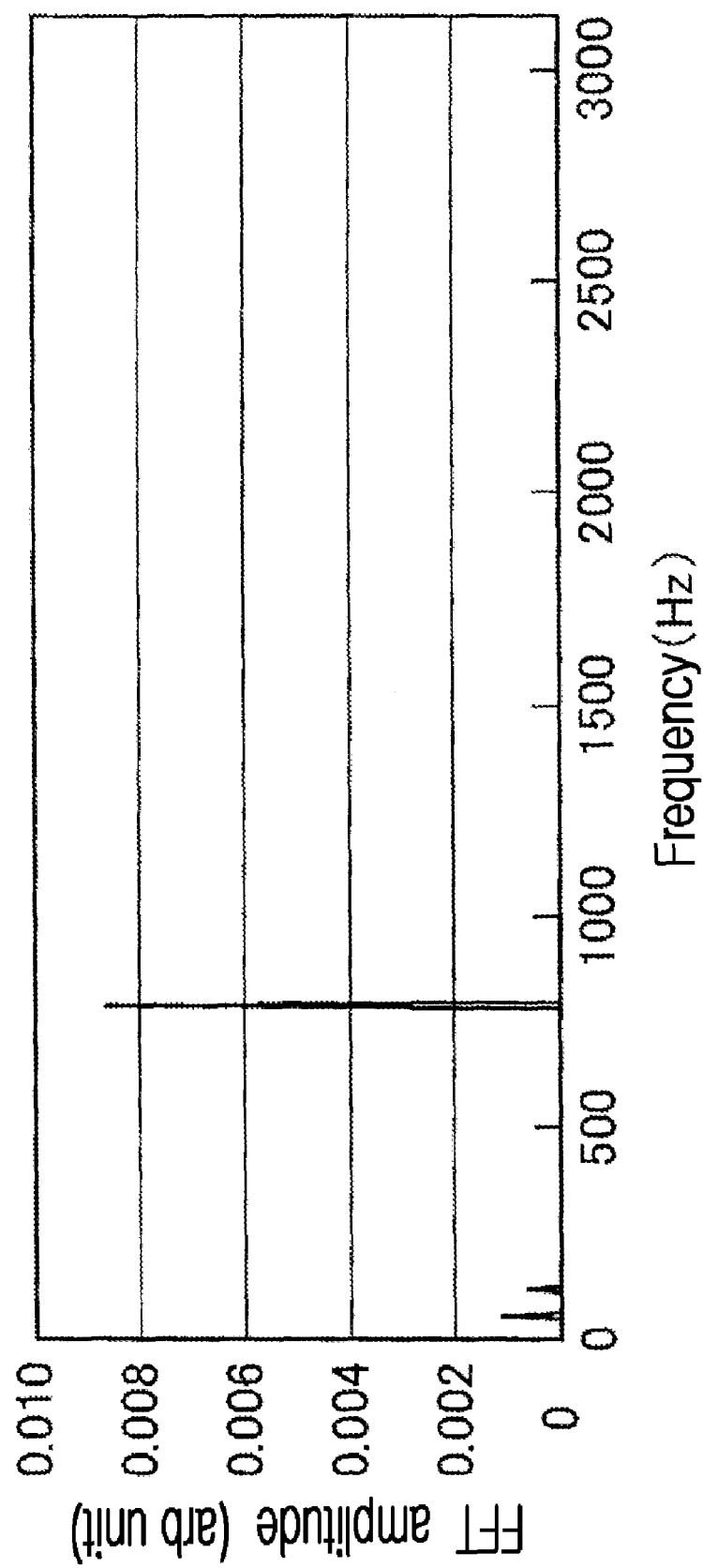
FIG. 5 is a graph showing an example of a frequency spectrum in the first embodiment.
Figure 6:
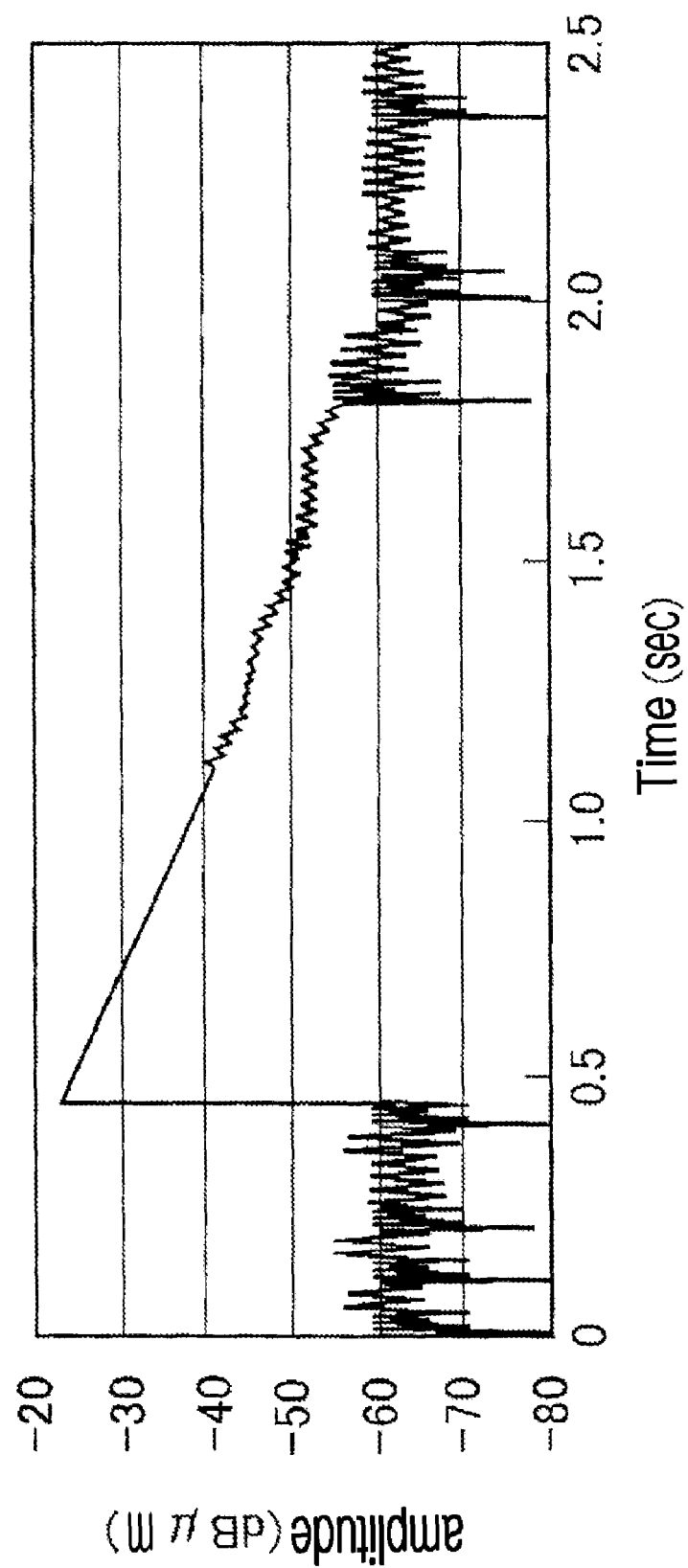
FIG. 6 is a graph showing a spectrum obtained by Hilbert transform in the first embodiment.

Results of Embodiment 1 are shown in FIGS. 4 through 6. FIG. 4 is a graph showing an damped vibration pattern. FIG. 5 is a graph showing an example of a frequency spectrum. FIG. 6 is a graph showing a spectrum obtained by using Hilbert transform.

The frequency spectrum of FIG. 5 is obtained by converting the damped vibration pattern in FIG. 4 by using Fourier transform. It is found from a peak value that a resonance frequency of the sample S is 787.7 Hz which is about the same as a resonance frequency of 780 Hz that is obtained by a method of scanning a frequency (with a minimum resolution of 10 Hz). It is found from a gradient of the graph in FIG. 6 that a Q value is 552.2.

Since the resonance frequency obtained by using the inspecting method according to the present embodiment is the same as that in case using conventional measuring method from Embodiment 1, it is found that the inspection method works. Also, the conventional measuring method obtained the Q value from a Full Width at Half Maximum (FWHM) of a resonance curve. If the Q value is high, since the number of measurement occasions is so small that reliability of measured values is low, the conventional measuring method doesn't work sometimes. However, the inspection method according to the present embodiment may works even in case that the Q value is high as in Embodiment 1.

Embodiment 2

Figure 7:
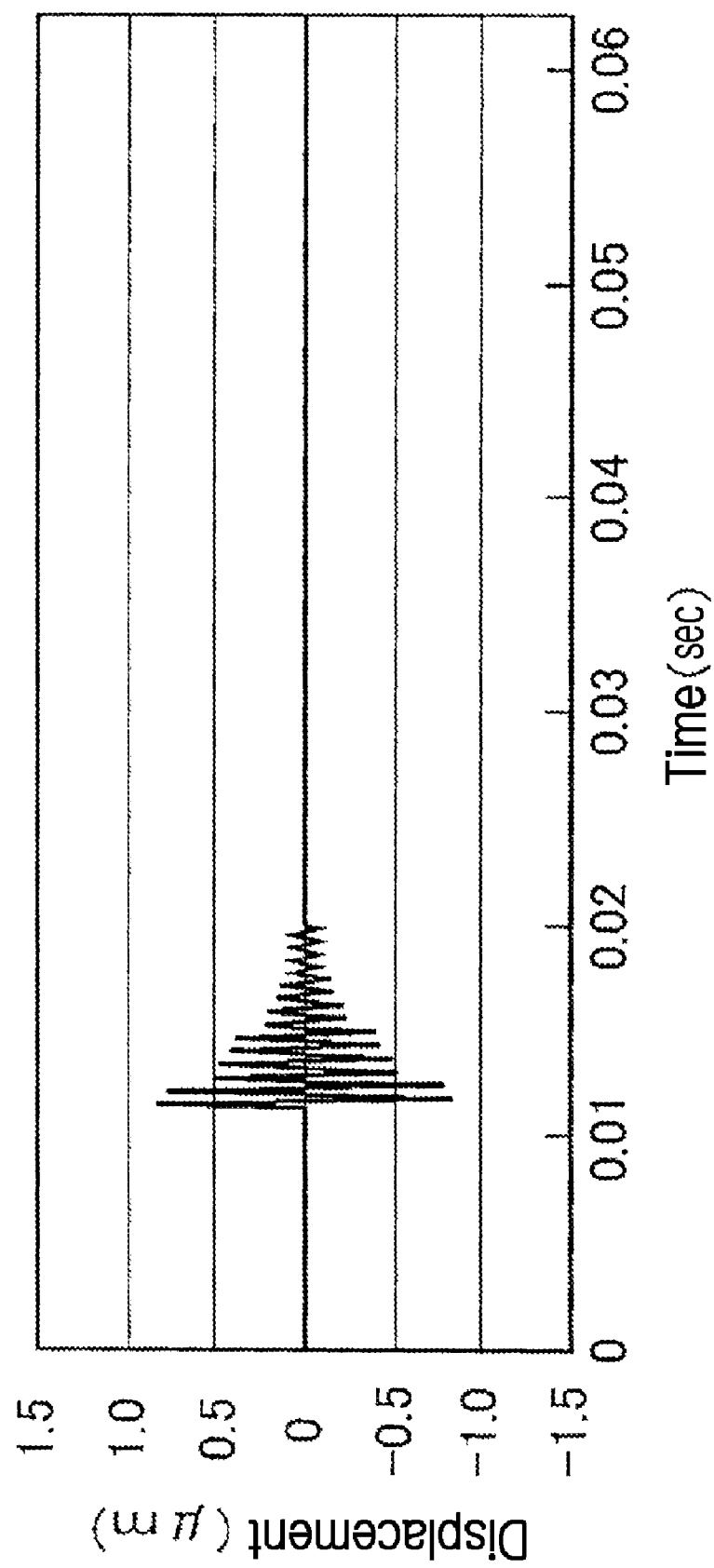
FIG. 7 is a graph showing an damped vibration pattern of a second embodiment.
Figure 8:
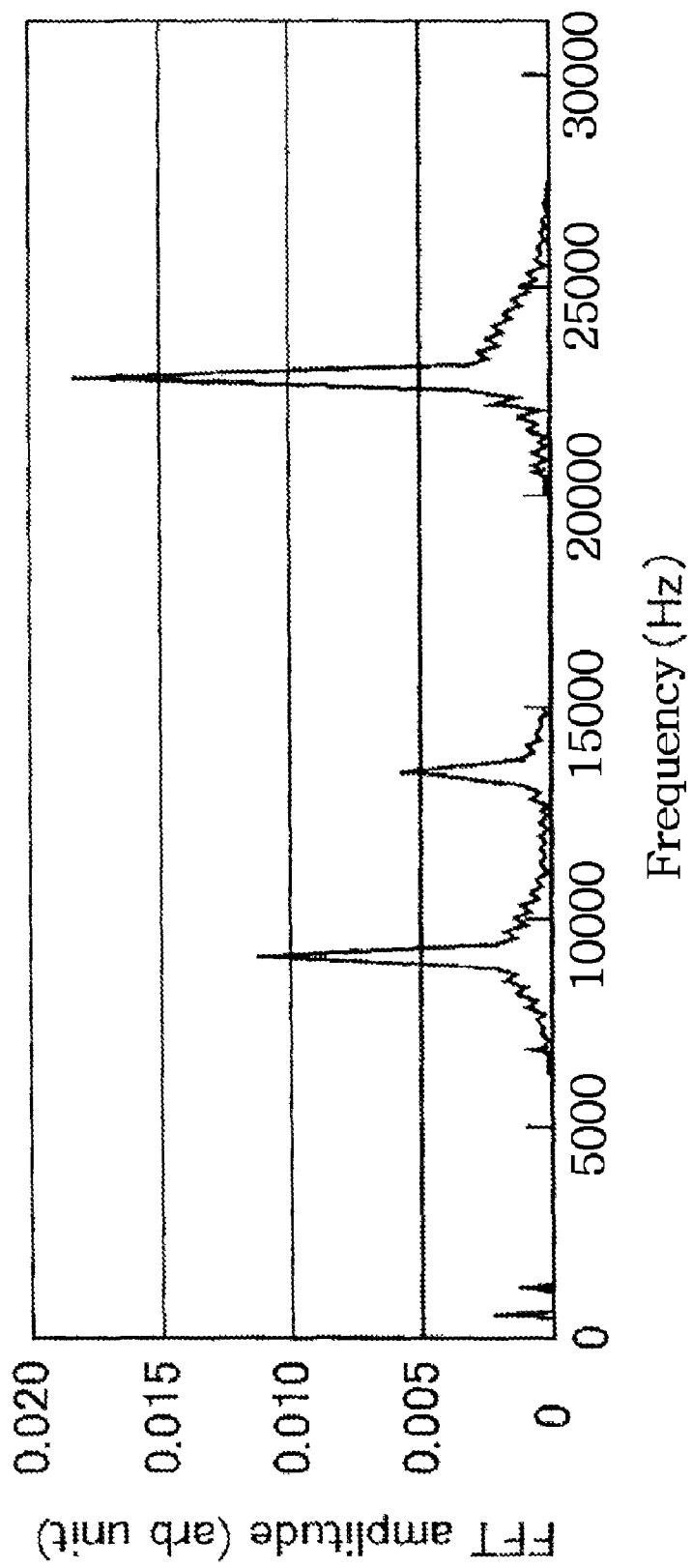
FIG. 8 is a graph showing an example of a frequency spectrum in the second embodiment.
Figure 9A:
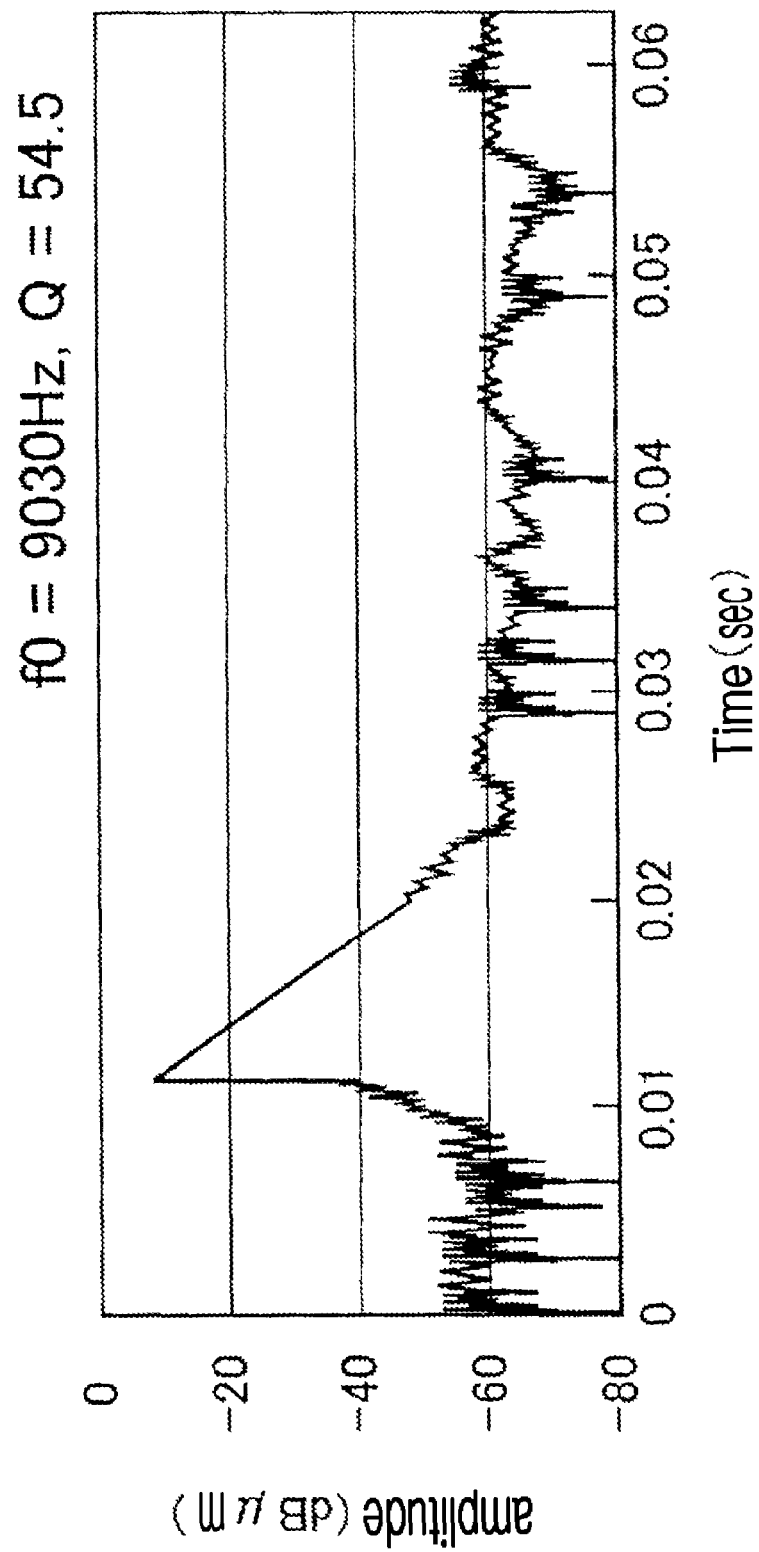
FIG. 9A is a first graph showing a spectrum obtained by Hilbert transform in the second embodiment.
Figure 9C:
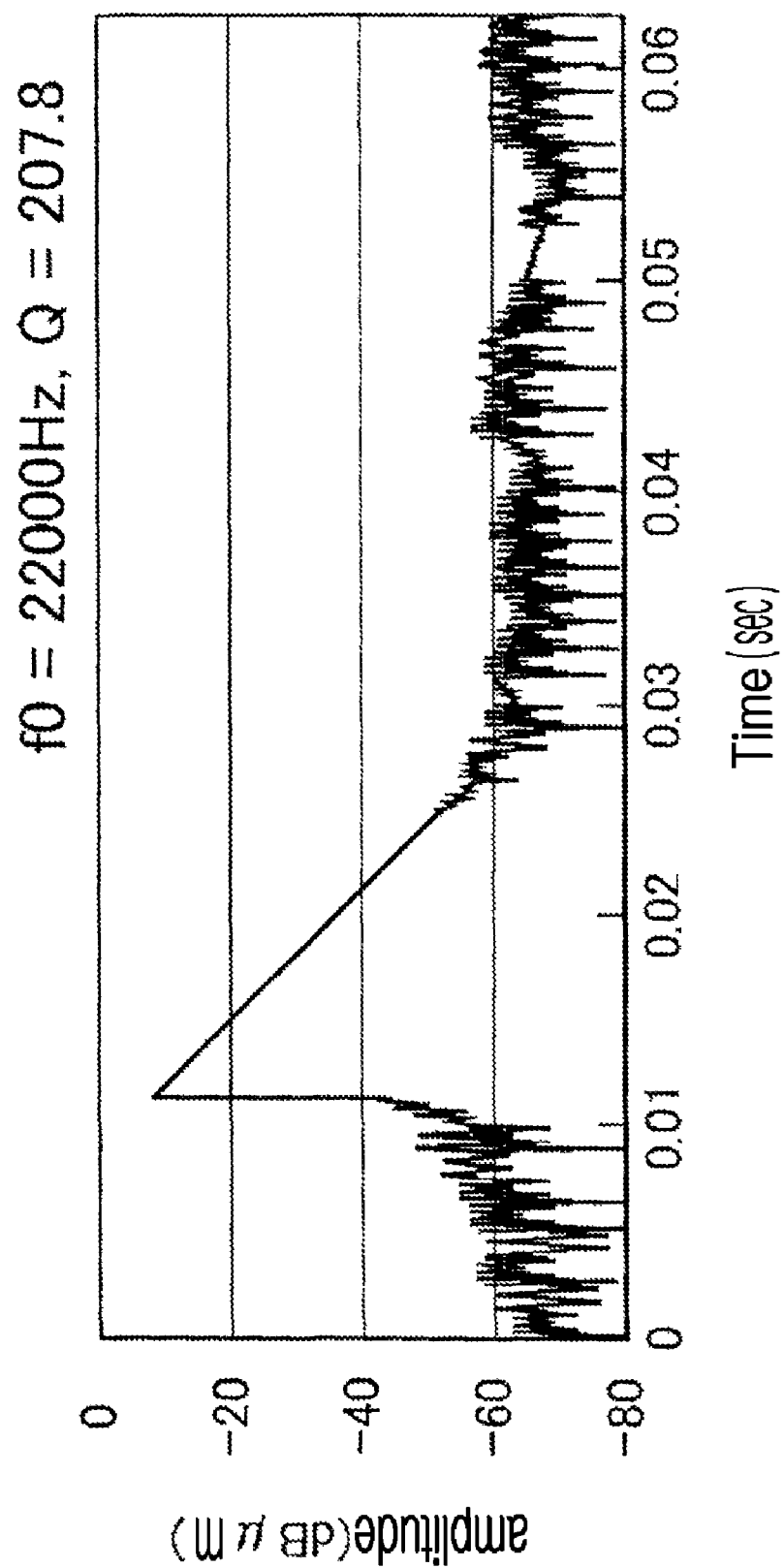
FIG. 9C is a third graph showing a spectrum obtained by Hilbert transform in the second embodiment.

Results of Embodiment 2 are shown in FIGS. 7, 8, 9A, 9B, and 9C. FIG. 7 is a graph showing an damped vibration pattern. FIG. 8 is a graph showing an example of a frequency spectrum. FIGS. 9A through 9C are graphs showing a spectrum obtained by using Hilbert transform.

From the number of peak values in the frequency spectrum of FIG. 8, which is obtained by converting the damped vibration pattern of FIG. 7 by using Fourier transform, it is found that there are 3 resonance frequencies. FIGS. 9A through 9C are graphs showing spectrums obtained by converting each of the frequencies of FIG. 8 by using Hilbert transform in order from least to greatest. As shown in FIG. 8, the three resonance frequencies are 9030 Hz, 13200 Hz, and 22000 Hz. Also, as shown in FIGS. 9A through 9C, a Q value is 54.5 in the case of the resonance frequency of 9030 Hz, 71.1 in the case of the resonance frequency of 13200 Hz, and 207.8 in the case of the resonance frequency of 22000 Hz.

The fishbone acoustic sensor, which is the sample S in Embodiment 2, is a microstructure having a complex structure in which a portion for receiving an input sound wave, a resonance portion that is supported with a cantilever, and a central line portion for connecting the portion for receiving the input sound wave to the resonance portion can move.

It is found from the results of Embodiment 2 that although the microstructure has the complex structure, the measuring method according to the present invention works. The conventional measuring method may not work or suffer a low degree of measurement precision due to the influence of vibration of a portion on other portions if the microstructure has a complex structure. Embodiment 2 can work, and can also identify a portion having defects since a natural frequency of each portion may be found as a resonance frequency.

The present application is based on Japanese Patent Application No. 2007-304597 filed on Nov. 26, 2007. The specification, claims, and drawings of Japanese Patent Application No. 2007-304597 are incorporated herein in its entirety by reference.

INDUSTRIAL APPLICABILITY

The present invention can be used as a device for inspecting a microstructure including a moving portion.

The invention claimed is:

1. A microstructure inspecting device which measures a damping characteristic value of a moving portion of a microstructure, the microstructure inspecting device comprising:
   an impact applying unit which applies an impact to the moving portion, the impact applying unit including a pressure wave generation device that is positioned to face and be spaced apart from the microstructure; and
   a measuring unit which measures a displacement of the moving portion without contacting the moving portion.

2. The microstructure inspecting device of claim 1, wherein the pressure wave generation device comprises a sound wave generating element of thermal excitation type, and a driving unit which inputs a pulse signal to the sound wave generating element.

3. The microstructure inspecting device of claim 2, wherein the sound wave generating element of thermal excitation type comprises:
   a thermally conductive substrate;
   a heat-insulating layer formed of nano-crystal silicon in one principal surface of the substrate;
   an insulating layer formed on the heat-insulating layer; and
   a conductive layer formed on the insulating layer and emitting heat when being supplied with current containing alternating current components.

4. A microstructure inspecting method comprising:
   applying an impact to a moving portion of a microstructure by using a pressure wave generating device that is positioned to face and be spaced apart from the microstructure;
   causing the moving portion to freely vibrate; and
   measuring a displacement of the moving portion without contacting the moving portion.

5. The microstructure inspecting method of claim 4, wherein the pressure wave generating device is a sound wave generating element of thermal excitation type.

6. The microstructure inspecting method of claim 5, wherein the sound wave generating element of thermal excitation type comprises:
   a thermally conductive substrate;
   a heat-insulating layer formed of nano-crystal silicon in one principal surface of the substrate;
   an insulating layer formed on the heat-insulating layer; and
   a conductive layer formed on the insulating layer and emitting heat when being supplied with current containing alternating current components.

7. The microstructure inspecting method of any one of claim 4, further comprising:
   calculating a Q value of the microstructure from the displacement of the moving portion measured in the measuring step; and
   determining that the microstructure is normal when the Q value is within a predetermined range, and determining that the microstructure is defective when the Q value is not within the predetermined range.

8. The microstructure inspecting method of claim 7, further comprising:
   feeding back the Q value calculated in the calculating step, and a determined result in the determining step to a control device that sets a manufacturing condition of a manufacturing device for manufacturing the microstructure.

* * * * *